United States Patent [19]
Berglund et al.

[11] Patent Number: 5,998,581
[45] Date of Patent: Dec. 7, 1999

[54] REDUCTIVE ALKYLATION OF GLYCOPEPTIDE ANTIBIOTICS

[75] Inventors: Richard Alan Berglund, Lafayette, Ind.; Nancy Anne Lockwood, Mountlake Terrace, Wash.; Howard Eugene Magadanz; Hua Zheng, both of Lafayette, Id.

[73] Assignee: Eli Lilly and Company, Indianapolis, Ind.

[21] Appl. No.: 09/290,204

[22] Filed: Apr. 12, 1999

Related U.S. Application Data

[62] Division of application No. 08/968,968, Nov. 12, 1997.

[60] Provisional application No. 60/031,596, Nov. 21, 1996.

[51] Int. Cl.$^6$ .......................... A61K 38/00; A61K 38/14; C07K 5/12
[52] U.S. Cl. .......................... 530/345; 530/317; 530/322; 530/333; 514/9
[58] Field of Search .................................... 530/345, 317, 530/322, 333; 514/9

[56] References Cited

U.S. PATENT DOCUMENTS

| | | | |
|---|---|---|---|
| 4,051,237 | 9/1977 | Kawaguchi et al. | 424/117 |
| 4,568,490 | 2/1986 | Umezawa et al. | 260/112 |
| 4,698,327 | 10/1987 | Nagarajan et al. | 514/8 |
| 5,312,738 | 5/1994 | Hammill et al. | 435/75 |

FOREIGN PATENT DOCUMENTS

| | | |
|---|---|---|
| 0 435 503 A1 | 7/1991 | European Pat. Off. . |
| 0 667 353 A1 | 8/1995 | European Pat. Off. . |

OTHER PUBLICATIONS

Tsuchiya, T., et al., *Tetrahedron Letters*, 51, 4951–4954 (1979).
Hanessian, S., et al., *Tetrahedron Letters*, 12, 1031–1034 (1978).
Abstracts of Papers, 210th ACS National Meeting, American Chemical Society, Chicago, Illinois, (Aug. 1995).
Nagabhushan, et al., *Carbohydrate Research,* vol. 130, pp. 243–249 (1984).
Cooper, et al., *The Journal of Antibiotics,* vol. 49, No. 6, pp. 575–581 (1996).
Wong, et al., *Analytical Biochemistry,* vol. 139, pp. 58–67 (1984).
Nagarajan, et al., *The Journal of Antibiotics,* vol. 42, No. 1, pp. 63–72 (1988).
Lee, et al., *Biochemestry,* vol. 28, pp. 1856–1861 (1989).
Popienick, et al., *J. Am. Chem. Soc.,* vol. 113, pp. 2264–2270 (1991).
Fultz, et al., *Electroanalysis,* vol. 3, pp. 519–526 (1991).
Nair, et al., *Chiralty,* pp. 590–595 (1996).

*Primary Examiner*—Michael P. Woodward
*Assistant Examiner*—Abdel A. Mohamed
*Attorney, Agent, or Firm*—Arlene K. Musser

[57] ABSTRACT

This invention is concerned with improved processes for reductive alkylation of glycopeptide antibiotics. The improvement residing in providing a source of copper which results in the initial production of a copper complex of the glycopeptide antibiotic. Reductive alkylation of this complex favors regioselective alkylation and increased yields. Copper complexes of the glycopeptide antibiotic starting materials and of the alkylated products are also part of the invention.

15 Claims, No Drawings

REDUCTIVE ALKYLATION OF GLYCOPEPTIDE ANTIBIOTICS

CROSS-REFERENCE

This application is a divisional of U.S. Ser. No. 08/968,968, filed Nov. 12, 1997 which claims the benefit of U.S. Provisional Application No. 60/031,596, filed Nov. 21, 1996.

BRIEF SUMMARY

The present invention is directed to improved methods for reductively alkylating glycopeptide antibiotics. The invention provides increased regioselectivity of reaction among multiple sites and thereby results in increased yields of the preferred product. In particular, the invention is directed to methods for preferentially conducting a reductive alkylation reaction on an amine on the saccharide of a glycopeptide antibiotic having one or more additional amines.

The essence of the invention is the discovery that conducting the reaction in the presence of soluble copper favors preferential reaction with the amine on the saccharide position, and thereby improves the yields of the reductive alkylation at this site. The initial step is the formation of a copper complex of the glycopeptide antibiotic, which subsequently undergoes the reductive alkylation. This invention is also directed to these copper complexes of the starting glycopeptide antibiotics. The alkylated glycopeptide antibiotic products are obtained as copper complexes, which are another embodiment of the present invention.

part. Two of these, vancomycin and teicoplanin, are sold as antibacterial products, but many others have been discovered and are being considered for development, especially since the emergence in the late 1980s of resistance to various antibiotics, including the glycopeptides themselves. The entire class of glycopeptide antibiotics is well described in "Glycopeptide Antibiotics", edited by Ramakrishnan Nagarajan (Marcel Dekker, Inc., New York, 1994). Among the more recently discovered glycopeptides are those known as A82846A (also called ereomomycin), A82846B (also known as chloroorienticin A), A82846C (also known as orienticin C), and orienticin A. The present invention is preferred for use with vancomycin type glycopeptide antibiotics, including vancomycin, A82846A, A82846B, A82846C, and orienticin A; the invention is especially preferred for use with A82846B.

Many modifications of naturally-occurring glycopeptides have been made. Among the modifications are reductive alkylations of reactive amine(s) in glycopeptides. See, for example, U.S. Pat. No. 4,698,327 describing reductive alkylations of vancomycin, and EPO 435 503 A1 and EPO 667 353 A1, both of which describe reductive alkylations of a variety of glycopeptides including vancomycin, A82846A, A82846B, A82846C, and orienticin A. These references describe reductive alkylations which introduce into the parent glycopeptides a great variety of alkyl groups.

U.S. Pat. No. 4,698,327 describes alkylated vancomycin compounds of the formula:

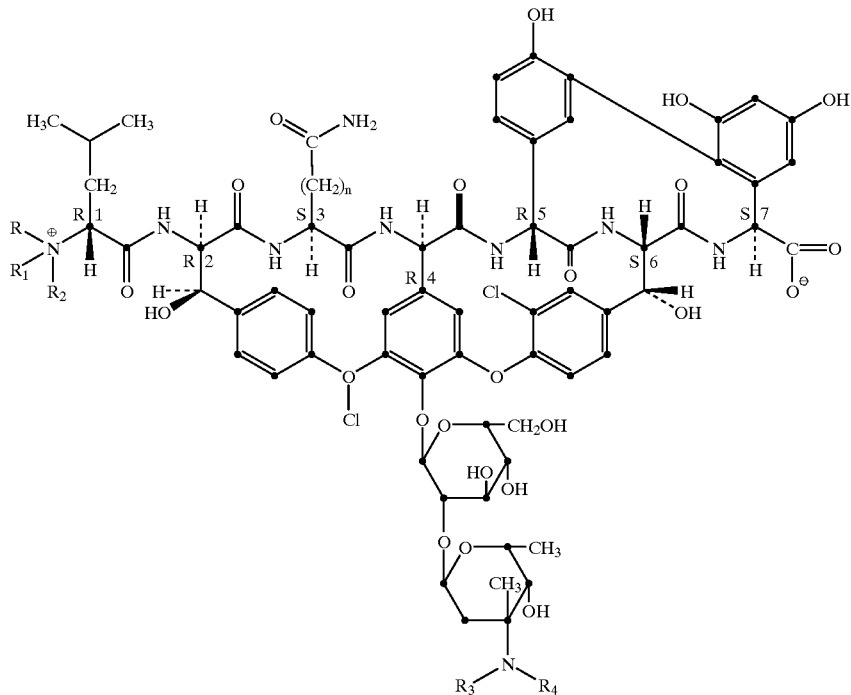

DETAILED DESCRIPTION

The present invention relates to reductive alkylation of glycopeptide antibiotics.

The glycopeptide antibiotics are a large class of substances either produced by microorganisms, or produced by microorganisms and thereafter subsequently modified in wherein R is hydrogen or methyl;

n is 1 or 2; and $R_1$ is hydrogen or methyl;

$R_2$ and $R_3$, independently, are hydrogen or a group of the formula: $R_6R_7CH-$;

$R_6$ and $R_7$ are independently $R_5$, $R_5$-($C_1$–$C_5$-alkyl) or $R_5$-($C_2$–$C_5$-alkenyl);

$R_5$ is hydrogen, $C_1$–$C_{10}$-alkyl, $C_2$–$C_{10}$-alkenyl, $C_1$–$C_4$ alkoxy, $C_3$–$C_{10}$-cycloalkyl, $C_5$–$C_{12}$-cycloalkenyl, phenyl, naphthyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N, and S, and $R_5$ may be substituted with one or more hydroxy, nitro, $C_1$–$C_{10}$-alkoxy, $C_1$–$C_{10}$-alkyl, phenyl, $C_1$–$C_6$-alkylthio, nitrile, halo, $C_2$–$C_4$-acylamino, amino, $C_1$–$C_4$-dialkylamino groups; and $R_4$ is hydrogen, provided that: (1) at least one of $R_2$ and $R_3$ must be other than hydrogen; (2) when n is 2, R must be hydrogen; (3) when R is methyl and $R_3$ is hydrogen, $R_2$ cannot be methyl and (4) when R and $R_1$ are both methyl, then $R_2$ is hydrogen or methyl and n is 1.

EPO 435 503 A1 is directed to alkylated and acylated glycopeptides of the formula:

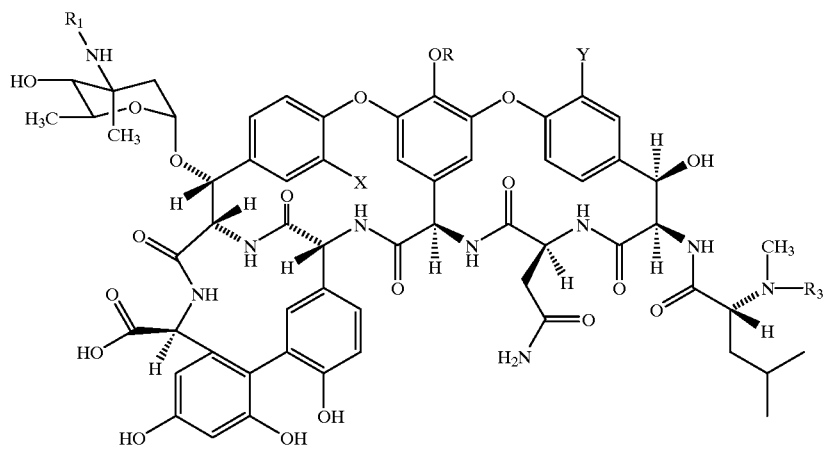

wherein:

R is hydrogen or a (4-epi-vancosaminyl)-O-glucosyl group of formula

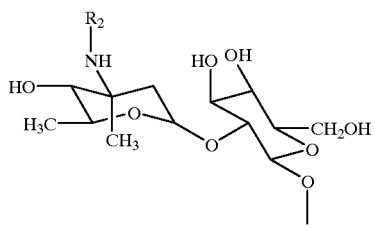

or the glucosyl group of formula

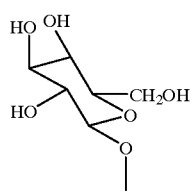

X is hydrogen or chloro;

Y is hydrogen or chloro;

$R_1$, $R_2$, and $R_3$ are independently hydrogen; $C_1$–$C_{12}$ alkyl; $C_2$–$C_9$ alkanoyl; or a group of formula

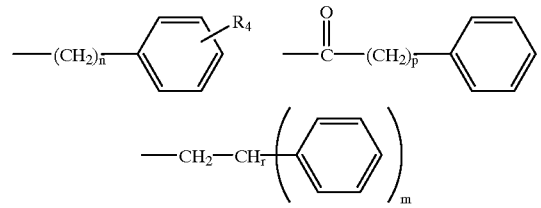

n is 1 to 3;

$R_4$ is hydrogen, halo, $C_1$–$C_8$ alkyl, $C_1$–$C_8$ alkoxy, or a group of formula

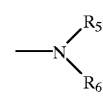

$R_5$ and $R_6$ are independently hydrogen or $C_1$–$C_3$ alkyl;

p is 0 to 2;

m is 2 or 3, and r=3−m; provided that, where R is a (4-epi-vancosaminyl)-O-glucosyl group, $R_1$, $R_2$, and $R_3$ are not all hydrogen, and where R is hydrogen or a glucosyl group, $R_1$ and $R_3$ are not both hydrogen.

Where R is (4-epi-vancosaminyl)-O-glucosyl, the glycopeptides so defined are

X=H, Y=Cl, A82846A

X=Y=Cl, A82846B

X=Y=H, A82846C

X=Cl, Y=H, orienticin A.

Thus, EPO 435 503 A1 describes alkyl derivatives of A82846A, A82846B, A82846C, and orienticin A wherein the alkyl group is

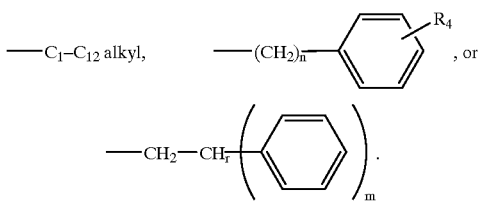

Preferred groups are $C_8$–$C_{12}$ alkyl and groups of the formula

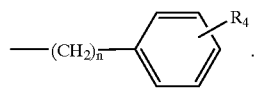

wherein $R_4$ is hydrogen, halo, $C_1$–$C_8$ alkyl, or $C_1$–$C_8$ alkoxy.

EPO 667 353 A1 describes alkylated glycopeptide antibiotics of the formula

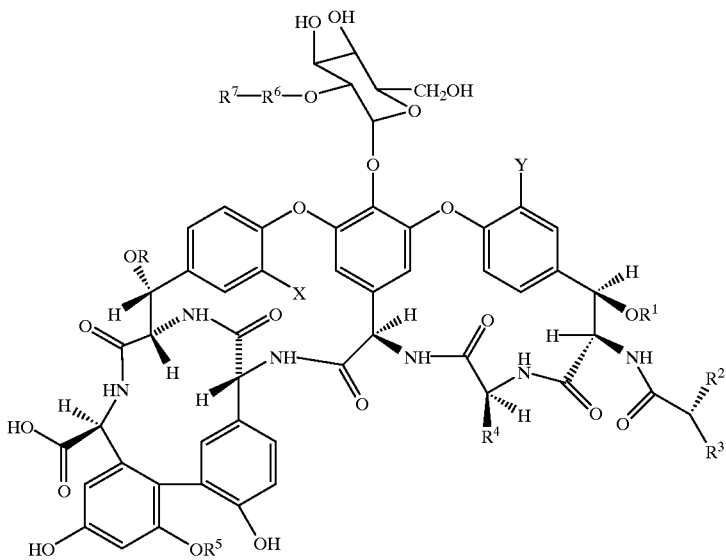

wherein:

X and Y are each independently hydrogen or chloro;

R is hydrogen, 4-epi-vancosaminyl, actinosaminyl, or ristosaminyl;

$R^1$ is hydrogen, or mannose;

$R^2$ is —$NH_2$, —$NHCH_3$, or —$N(CH_3)_2$;

$R^3$ is —$CH_2CH(CH_3)_2$, [p-OH, m-Cl]phenyl, p-rhamnose-phenyl, or [p-rhamnose-galactose]phenyl, [p-galactose-galactose]phenyl, [p-$CH_3$O-rhamnose]phenyl;

$R^4$ is —$CH_2(CO)NH_2$, benzyl, [p-OH]phenyl, or [p-OH, m-Cl]phenyl;

$R^5$ is hydrogen, or mannose;

$R^6$ is vancosaminyl, 4-epi-vancosaminyl, L-acosaminyl, L-ristosaminyl, or L-actinosaminyl;

$R^7$ is ($C_2$–$C_{16}$)alkenyl, ($C_2$–$C_{12}$)alkynyl, ($C_1$–$C_{12}$ alkyl)-$R_8$, ($C_1$–$C_{12}$ alkyl)-halo, ($C_2$–$C_6$ alkenyl)-$R_8$, ($C_2$–$C_6$ alkynyl)-$R_8$, ($C_1$–$C_{12}$ alkyl)-O-$R_8$, and is attached to the amino group of $R^6$;

$R^8$ is selected from the group consisting of:

a) multicyclic aryl unsubstituted or substituted with one or more substituents independently selected from the group consisting of:

(i) hydroxy,
(ii) halo,
(iii) nitro,
(iv) ($C_1$–$C_6$)alkyl,
(v) ($C_2$–$C_6$)alkenyl,
(vi) ($C_2$–$C_6$)alkynyl,
(vii) ($C_1$–$C_6$)alkoxy,
(viii) halo-($C_1$–$C_6$)alkyl,
(ix) halo-($C_1$–$C_6$)alkoxy,
(x) carbo-($C_1$–$C_6$)alkoxy,
(xi) carbobenzyloxy,
(xii) carbobenzyloxy substituted with ($C_1$–$C_6$)alkyl, ($C_1$–$C_6$)alkoxy, halo, or nitro,
(xiii) a group of the formula —$S(O)_{n'}$—$R^9$, wherein n' is 0–2 and $R^9$ is ($C_1$–$C_6$)alkyl, phenyl, or phenyl substituted with ($C_1$–$C_6$)alkyl, ($C_1$–$C_6$)alkoxy, halo, or nitro, and
(xiv) a group of the formula —$C(O)N(R^{10})_2$ wherein each $R^{10}$ substituent is independently hydrogen, ($C_1$–$C_6$)-alkyl, ($C_1$–$C_6$)-alkoxy, phenyl, or phenyl substituted with ($C_1$–$C_6$)-alkyl, ($C_1$–$C_6$)-alkoxy, halo, or nitro;

b) heteroaryl unsubstituted or substituted with one or more substituents independently selected from the group consisting of:

(i) halo,
(ii) ($C_1$–$C_6$)alkyl,
(iii) ($C_1$–$C_6$)alkoxy,
(iv) halo-($C_1$–$C_6$)alkyl,
(v) halo-($C_1$–$C_6$)alkoxy,
(vi) phenyl,
(vii) thiophenyl,
(viii) phenyl substituted with halo, ($C_1$–$C_6$)alkyl, ($C_2$–$C_6$) alkenyl, ($C_2$–$C_6$)alkynyl, ($C_1$–$C_6$)alkoxy, or nitro,
(ix) carbo-($C_1$–$C_6$)alkoxy,
(x) carbobenzyloxy,
(xi) carbobenzyloxy substituted with ($C_1$–$C_6$)alkyl, ($C_1$–$C_6$) alkoxy, halo, or nitro,
(xii) a group of the formula —$S(O)_{n'}$—$R^9$, as defined above, (xiii) a group of the formula —C(O)N(R$^{10}$)$_2$ as defined above, and (xiv) thienyl;

c) a group of the formula:

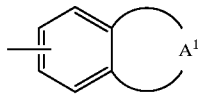

wherein A$^1$ is —OC(A$^2$)$_2$—C(A$^2$)$_2$—O—, —O—C(A$^2$)$_2$—O—, —C(A$^2$)$_2$—O—, or —C(A$^2$)$_2$—C(A$^2$)$_2$—C(A$^2$)$_2$—C(A$^2$)$_2$—, and each A$^2$ substituent is independently selected from hydrogen, (C$_1$–C$_6$)-alkyl, (C$_1$–C$_6$)alkoxy, and (C$_4$–C$_{10}$)cycloalkyl;

d) a group of the formula:

wherein p is from 1 to 5; and

R$^{11}$ is independently selected from the group consisting of:

(i) hydrogen,
(ii) nitro,
(iii) hydroxy,
(iv) halo,
(v) (C$_1$–C$_8$)alkyl,
(vi) (C$_1$–C$_8$)alkoxy,
(vii) (C$_9$–C$_{12}$)alkyl,
(viii) (C$_2$–C$_9$)alkynyl,
(ix) (C$_9$–C$_{12}$)alkoxy,
(x) (C$_1$–C$_3$)alkoxy substituted with (C$_1$–C$_3$)alkoxy, hydroxy, halo(C$_1$–C$_3$)alkoxy, or (C$_1$–C$_4$)alkylthio,
(xi) (C$_2$–C$_5$)alkenyloxy,
(xii) (C$_2$–C$_{13}$)alkynyloxy
(xiii) halo-(C$_1$–C$_6$)alkyl,
(xiv) halo-(C$_1$–C$_6$)alkoxy,
(xv) (C$_2$–C$_6$)alkylthio,
(xvi) (C$_2$–C$_{10}$)alkanoyloxy,
(xvii) carboxy-(C$_2$–C$_4$)alkenyl,
(xviii) (C$_1$–C$_3$)alkylsulfonyloxy,
(xix) carboxy-(C$_1$–C$_3$)alkyl,
(xx) N-[di(C$_1$–C$_3$)-alkyl]amino-(C$_1$–C$_3$)alkoxy,
(xxi) cyano-(C$_1$–C$_6$)alkoxy, and
(xxii) diphenyl-(C$_1$–C$_6$)alkyl, with the proviso that when R$^{11}$ is (C$_1$–C$_8$)alkyl, (C$_1$–C$_8$) alkoxy, or halo, p must be greater or equal to 2, or when R$^7$ is (C$_1$–C$_3$ alkyl)-R$^8$ then R$^{11}$ is not hydrogen, (C$_1$–C$_8$)alkyl, (C$_1$–C$_8$)alkoxy, or halo;

e) a group of the formula:

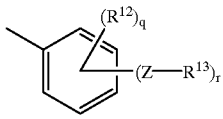

wherein q is 0 to 4;

R$^{12}$ is independently selected from the group consisting of:

(i) halo,
(ii) nitro,
(iii) (C$_1$–C$_6$)alkyl,
(iv) (C$_1$–C$_6$)alkoxy,
(v) halo-(C$_1$–C$_6$)alkyl,
(vi) halo-(C$_1$–C$_6$)alkoxy, and
(vii) hydroxy, and
(vii) (C$_1$–C$_6$)thioalkyl;

r is 1 to 5; provided that the sum of q and r is no greater than 5;

Z is selected from the group consisting of:

(i) a single bond,
(ii) divalent (C$_1$–C$_6$)alkyl unsubstituted or substituted with hydroxy, (C$_1$–C$_6$)alkyl, or (C$_1$–C$_6$)alkoxy,
(iii) divalent (C$_2$–C$_6$)alkenyl,
(iv) divalent (C$_2$–C$_6$)alkynyl, or
(v) a group of the formula —(C(R$^{14}$)$_2$)$_s$—R$^{15}$— or —R$^{15}$—(C(R$^{14}$)$_2$)$_s$—, wherein s is 0–6; wherein each R$^{14}$ substituent is independently selected from hydrogen, (C$_1$–C$_6$)-alkyl, or (C$_4$–C$_{10}$) cycloalkyl; and R$^{15}$ is selected from —O—, —S—, —SO—, —SO$_2$—, —SO$_2$—O—, —C(O)—, —OC(O)—, —C(O)O—, —NH—, —N(C$_1$–C$_6$ alkyl)-, and —(C(O)NH—, —NHC(O)—, N=N;

R$^{13}$ is independently selected from the group consisting of:

(i) (C$_4$–C$_{10}$)heterocyclyl,
(ii) heteroaryl,
(iii) (C$_4$–C$_{10}$)cycloalkyl unsubstituted or substituted with (C$_1$–C$_6$)alkyl, or
(iv) phenyl unsubstituted or substituted with 1 to 5 substituents independently selected from: halo, hydroxy, nitro, (C$_1$–C$_{10}$)alkyl, (C$_1$–C$_{10}$)alkoxy, halo-(C$_1$–C$_3$)alkoxy, halo-(C$_1$–C$_3$)alkyl, (C$_1$–C$_3$) alkoxyphenyl, phenyl, phenyl-(C$_1$–C$_3$)alkyl, (C$_1$–C$_6$) alkoxyphenyl, phenyl-(C$_2$–C$_3$)alkynyl, and (C$_1$–C$_6$) alkylphenyl;

f) (C$_4$–C$_{10}$)cycloalkyl unsubstituted or substituted with one or more substituents independently selected from the group consisting of:

(i) (C$_1$–C$_6$)alkyl,
(ii) (C$_1$–C$_6$)alkoxy,
(iii) (C$_2$–C$_6$)alkenyl,
(iv) (C$_2$–C$_6$)alkynyl, (V) (C$_4$–C$_{10}$) cycloalkyl,
(vi) phenyl,
(vii) phenylthio,
(viii) phenyl substituted by nitro, halo, (C$_1$–C$_6$) alkanoyloxy, or carbocycloalkoxy, and
(ix) a group represented by the formula —Z—R$^{13}$ wherein Z and R$^{13}$ are as defined above; and g) a group of the formula:

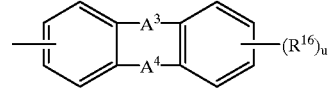

wherein
A$^3$ and A$^4$ are each independently selected from
(i) a bond,
(ii) —O—,
(iii) —S(O)$_t$—, wherein t is 0 to 2, (iv) —C(R$^{17}$)$_2$—, wherein each R$^{17}$ substituent is independently selected from hydrogen, (C$_1$–C$_6$)alkyl, hydroxy, (C$_1$–C$_6$)alkyl, (C$_1$–C$_6$)alkoxy, or both R$^{17}$ substituents taken together are O, (v) —N(R$^{18}$)$_2$—, wherein each R$^{18}$ substituent is independently selected from hydrogen; (C$_1$–C$_6$)alkyl; (C$_2$–C$_6$)alkenyl; (C$_2$–C$_6$)alkynyl; (C$_4$–C$_{10}$)cycloalkyl; phenyl; phenyl substituted by nitro, halo, (C$_1$–C$_6$) alkanoyloxy; or both R$^{18}$ substituents taken together are (C$_4$–C$_{10}$)cycloalkyl;

R$^{16}$ is R$^{12}$ or R$^{13}$ as defined above; and u is 0–4.

In this reference, preferred glycopeptide antibiotics are A82846A, A82846B, A82846C, and orienticin A; preferred alkyls are those wherein R$^7$ is CH$_2$—R$_8$; and preferred R$^8$ moieties are those defined as groups "(d)" and "(e)".

The present invention can be utilized to make the alkylated glycopeptides described in these references. Preferred alkylated glycopeptides which can be prepared by the present process include the following:

N$^4$-n-octylA82846B
N$^4$-n-decylA82846B
N$^4$-benzylA82846B
N$^4$-(p-chlorobenzyl)A82846B
N$^4$-(p-bromobenzyl)A82846B
N$^4$-(p-propylbenzyl)A82846B
N$^4$-(p-isopropylbenzyl)A82846B
N$^4$-(p-butylbenzyl)A82846B
N$^4$-(p-isobutylbenzyl)A82846B
N$^4$-(p-pentylbenzyl)A82846B
N$^4$-(p-isohexylbenzyl)A82846B
N$^4$-(p-octylbenzyl)A82846B
N$^4$-(p-propoxybenzyl)A82846B
N$^4$-(p-isopropoxybenzyl)A82846B
N$^4$-(p-butoxybenzyl)A82846B
N$^4$-(p-tert-butoxybenzyl)A82846B
N$^4$-(p-pentyloxybenzyl)A82846B
N$^4$-(p-hexyloxybenzyl)A82846B
N$^4$-(o-hexyloxybenzyl)A82846B
N$^4$-(p-heptyloxybenzyl)A82846B
N$^4$-(p-octyloxybenzyl)A82846B
N$^4$-phenethylA82846B
N$^4$-(4-phenylbenzyl)A82846B
N$^4$-(4-(4-chlorophenyl)benzylA82846B
N$^4$-(4-(4-methylbenzyloxy)benzyl)A82846B
N$^4$-(4-(4-ethylbenzyloxy)benzyl)A82846B
N$^4$-(4-(4-chlorophenethyl)benzyl)A82846B
N$^4$-(4-(2-(4-methoxyphenyl)ethynyl)benzyl)A82846B.

The references noted above describe the reductive alkylation as comprising a first step, in which the glycopeptide is reacted with the respective aldehyde or ketone to form a Schiff's base, which in a second step is reduced to the desired alkylated product. In one variation of this procedure, EPO 667 353 A1 describes a process in which the reducing agent is added simultaneously with the glycopeptide and aldehyde or ketone. The references say that any chemical reducing agent can be employed, but the references also suggest a preference for sodium cyanoborohydride.

Essentially all glycopeptides contain multiple reactive sites. Manipulation of these multiple sites is not uniformly advantageous. It is sometimes desired to react the glycopeptide regioselectivity, to have the reaction occur at only one of multiple sites. This is equally true in the case of reductive alkylations of glycopeptides. An example of this is A82846B. While derivatives alkylated on the leucine amine (N$^1$) and/or the monosaccharide (N$^6$) are active as antibacterials, alkylation of the N$^4$ (disaccharide) amine appears to be preferred. Pharmaceutical practices require a relatively pure form, and therefore preferential reaction of the N$^4$ site is desirable in order to achieve a highly pure N$^4$-alkylated product.

The present invention provides a technique for obtaining reaction preferentially on the amine on a saccharide at the N$^4$ position in the glycopeptide antibiotic. In the case of vancomycin, A82846A, A82846B, A82846C, and orienticin A, the present process reduces reactivity at sites N$^1$ and N$^6$ and thereby increases reaction selectivity for the N$^4$ (disaccharide) site. The invention requires the initial preparation of a soluble copper complex of the glycopeptide, which is then reductively alkylated. The soluble copper complex is achieved by reacting the glycopeptide antibiotic with copper, typically by adding a source of soluble copper to a reaction mixture containing the glycopeptide antibiotic. The identity of the copper source is not critical, so long as it is at least partially soluble and does not negatively impact the pH. Such a copper salt can be used in anhydrous or hydrated form. A preferred source of copper is copper (II) acetate, most conveniently employed as the hydrate.

Supplying copper to the reaction mixture results in the initial production of a copper complex with the glycopeptide antibiotic starting material, typically in a 1:1 ratio. This copper complex of the glycopeptide antibiotic starting material is one of the features of the present invention.

The reducing agent to be employed in the present invention is sodium cyanoborohydride or pyridine.borane complex.

The identity of the solvent is important. Straight methanol has given high yields, and it is expected that methanol somewhat diluted as with DMF or DMSO would provide acceptable yields. Other solvents have not produced satisfactory results. Therefore, the reaction solvent is at least predominantly methanol.

The reaction should be conducted at a pH of 6–8, and preferably at a pH of 6.3–7.0.

The amounts of reactants and reagents to be employed are not critical; amounts to maximize the yield of product will vary somewhat with the identity of the reactants. The reaction consumes the glycopeptide antibiotic and the aldehyde or ketone in equimolar amounts. A slight excess of the aldehyde or ketone, e.g., 1.3 to 1.7:1, is preferred. The amount of the glycopeptide antibiotic to be used must be corrected for its purity. The reaction consumes an equimolar amount of the reducing agent. At least that amount should be employed, and a slight excess is preferred. The amount of soluble copper is not critical when employing sodium cyanoborohydride as reducing agent. When employing pyridine.borane as reducing agent, the amount of soluble copper to be employed is more important, since excess copper will react with the pyridine.borane. Regardless of the identity of the reducing agent, the present process first results in the formation of a 1:1 complex with the glycopeptide antibiotic; therefore, the copper is preferably present in an amount approximately equimolar with the glycopeptide antibiotic. Amounts exceeding one molar equivalent (in the case of pyridine.borane) or two molar equivalents (in the case of sodium cyanoborohydride) are undesirable.

Summarizing the foregoing, the ideal amounts to be employed are a ratio of:
glycopeptide:aldehyde or ketone:reducing agent:copper salt of:

1:1.3 to 1.5:1.3:1 with the exception that when using pyridine.borane complex as reducing agent, the preferred ratio is:

1:1.3 to 1.7:1.5:0.9 to 1.0.

The concentration of the reactants in the solvent has some bearing on the process. Methanol volume relative to mass of glycopeptide antibiotic can vary from 50:1 to 500:1; a 100:1 dilution appears to be a useful, practical ratio, although higher dilutions may give slightly higher yields.

The temperature at which the process is carried out is not critical. Reaction mixtures in methanol boil at about 67° C., thereby setting the maximum temperature when employing straight methanol as the solvent. Higher temperatures are of course possible when employing mixtures of methanol or when operating under pressure. Lower temperatures can be tolerated, but preferably not lower than about 45° C. The ideal condition for sodium cyanoborohydride as reducing agent is the use of straight methanol and conducting the reaction at reflux; the ideal condition for pyridine.borane as reducing agent is also the use of straight methanol but at temperatures of about 58–63° C.

Some product is produced with even short reaction times. Longer reaction times, such as from 6 hours to 48 hours, are preferred. However, the ideal reaction time appears to be approximately 20 to 25 hours. Longer times may increase the yield of products alkylated at undesired sites in the glycopeptide antibiotic.

In carrying out the present invention, the glycopeptide antibiotic and copper are preferably mixed in a solvent, creating the soluble copper complex of the glycopeptide antibiotic, and the aldehyde and reducing agents are then added. However, the precise order of addition is not critical. Portionwise addition of the reducing agent is preferred, and is required for good results when employing pyridine.borane complex as reducing agent. The reaction is continued for a period of time, after which the product is produced and can be separated from the reaction mixture.

Upon the completion of the reaction period, the reaction mixture is preferably quenched, as by the addition of sodium borohydride. This reagent consumes residual aldehyde or ketone and thereby prevents further undesired reactions.

The product is isolated from the reaction mixture as a copper complex of the alkylated glycopeptide. Isolation is achieved by concentration of the reaction mixture and precipitation of the complex by addition of an antisolvent such as ethyl acetate, acetone, 1-propanol, isopropyl alcohol, or preferably acetonitrile. The complex can be broken by aqueous treatment at pH $^2$4, freeing the simple alkylated glycopeptide product, which can, if desired, be purified in conventional manner.

The following examples illustrate the present invention and will enable those skilled in the art to practice the same.

REFERENCE EXAMPLE A (NO COPPER)

A82846B (6.0 g, 76.5% potency, 4.59 bg, 2.88 mmol), 4'-chloro-4-biphenylcarboxaldehyde (0.86 g, 3.97 mmol), and sodium cyanoborohydride (84 mg, 1.34 mmol) were added to 600 mL methanol and the solution was heated at reflux for 3 hours. An additional portion of sodium cyanoborohydride (84 mg, 1.34 mmol) was added and the mixture was heated 3 hours longer at reflux. A final portion of sodium cyanoborohydride (84 mg, 1.34 mmol) was added and heating at reflux was continued an additional 17 hours. The clear colorless solution was cooled to ambient temperature and concentrated to 130 mL on a rotary evaporator. The product was precipitated by addition of 200 mL of isopropyl alcohol over 2 hours. After cooling to 0° C. and stirring 1 hour, filtration afforded $N^4$-(4-(4-chlorophenyl)benzyl) A82846B as a white solid (5.61 g, 49.3% potency, 2.77 bg, 53.7%).

EXAMPLE 1

A82846B(0.50 g, 76.3% potency, 0.38 bg, 0.24 mmol), 4'-chloro-4-biphenylcarboxaldehyde (70 mg, 0.32 mmol), and cupric acetate monohydrate (51 mg, 0.26 mmol) were stirred in 50 mL methanol. Sodium cyanoborohydride (20 mg, 0.32 mmol) was added and the solution was heated at reflux for 23 hours. The clear purple solution was cooled to ambient temperature and 12% sodium borohydride in aqueous 14 M sodium hydroxide (0.03 mL, 0.14 mmol) was added. One drop of acetic acid was added to pH adjust the solution to 7.3. An additional portion of 12% sodium borohydride in aqueous 14 M sodium hydroxide (0.23 mL, 0.10 mmol) was added followed by one drop of acetic acid to maintain the solution pH at 7.3. The mixture was stirred at ambient temperature for 1 hour and concentrated to 12 mL on a rotary evaporator. The product was precipitated by addition of 25 mL of acetonitrile over 20 min. After stirring 20 min at ambient temperature, filtration afforded the copper complex of $N^4$-(4-(4-chlorophenyl)benzyl)A82846B as a purple solid (0.58 g, potency 59.5%, 0.35 bg, 80.3%).

EXAMPLE 2

A82846B (6.0 g, 78.4% potency, 4.7 bg, 2.95 mmol), was stirred in 600 mL methanol and cupric acetate (0.66 g, 3.6 mmol) was added. After stirring at ambient temperature for 15 min, 4'-chloro-4-biphenylcarboxaldehyde (0.95 g, 4.4 mmol), and sodium cyanoborohydride (0.27 g, 4.3 mmol) were added and the mixture was heated at reflux for 24 hours. After cooling to ambient temperature, HPLC analysis of a reaction aliquot afforded a yield of 4.52 g (85.4%) of $N^4$-(4-(4-chlorophenyl)benzyl)A82846B.

EXAMPLE 3

A82846B (2.5 g, 78.5% potency, 1.96 bg, 1.23 mmol), was stirred in 250 mL methanol and cupric acetate monohydrate (0.26 g, 1.32 mmol) was added. After stirring at ambient temperature for 10 min, 4'-chloro-4-biphenylcarboxaldehyde (0.35 g, 1.6 mmol), and sodium cyanoborohydride (34 mg, 0.54 mmol) were added and the mixture was heated at reflux for 3 hours. An additional portion of sodium cyanoborohydride (34 mg, 0.54 mmol) was added and the mixture was heated 3 hours longer at reflux. A final portion of sodium cyanoborohydride (34 mg, 0.54 mmol) was added and heating at reflux continued an additional 17 hours. The mixture was cooled to ambient temperature and 12% sodium borohydride in aqueous 14 M sodium hydroxide (0.14 mL, 0.63 mmol) was added. A few drops of acetic acid were added to pH adjust the solution to 7.3. A second portion of 12% sodium borohydride in aqueous 14 M sodium hydroxide (0.13 mL, 0.6 mmol) was added and a few drops of acetic acid were added to adjust the solution pH to 8.1. After stirring at ambient temperature for 2 hours, the reaction mixture was concentrated to 60 mL on a rotary evaporator. Isopropyl alcohol (175 mL) was added dropwise over a period of 1 hour to precipitate the copper complex of $N^4$-(4-(4-chlorophenyl)benzyl)A82846B. Filtration afforded the complex as a purple solid (6.50 g, 26.9% potency as wet cake, 1.75 bg, 79.1%).

EXAMPLE 4

A82846B (2.5 g, 78.5% potency, 1.96 bg, 1.23 mmol), was stirred in 250 mL methanol and cupric acetate monohydrate (0.26 g, 1.32 mmol) was added. After stirring at ambient temperature for 10 min, 4'-chloro-4-biphenylcarboxaldehyde (0.35 g, 1.6 mmol), and sodium cyanoborohydride (34 mg, 0.54 mmol) were added and the mixture was heated at reflux for 3 hours. An additional portion of sodium cyanoborohydride (34 mg, 0.54 mmol) was added and the mixture was heated 3 hours longer at reflux. A final portion of sodium cyanoborohydride (34 mg, 0.54 mmol) was added and heating at reflux continued an additional 17 hours. The mixture was cooled to ambient temperature and 12% sodium borohydride in aqueous 14 M sodium hydroxide (0.14 mL, 0.63 mmol) was added. A few drops of acetic acid were added to pH adjust the solution to 7.3. A second portion of 12% sodium borohydride in aqueous 14 M sodium hydroxide (0.13 mL, 0.6 mmol) was added and a few drops of acetic acid were added to adjust the solution pH to 8.2. After stirring at ambient temperature for 1.5 hours, the reaction mixture was concentrated to 60 mL on a rotary evaporator. Isopropyl alcohol (175 mL) was added dropwise over a period of 1 hour to precipitate the product. It was filtered and dried in vacuo to afford the copper complex of $N^4$-(4-(4-chlorophenyl)benzyl)A82846B as a purple solid (2.56 g, 62.9% potency, 1.61 bg, 72.9%).

EXAMPLE 5

A82846B (6.0 g, 76.1% potency, 4.56 bg, 2.9 mmol), was stirred in 600 mL methanol and cupric acetate monohydrate (0.63 g, 3.15 mmol) was added. After stirring at ambient temperature for 15 min, 4'-chloro-4-biphenylcarboxaldehyde (0.85 g, 3.9 mmol), and sodium cyanoborohydride (84 mg, 1.3 mmol) were added and the mixture was heated at reflux for 3 hours. An additional portion of sodium cyanoborohydride (84 mg, 1.3 mmol) was added and the mixture was heated 3 hours longer at reflux. A final portion of sodium cyanoborohydride (84 mg, 1.3 mmol) was added and heating at reflux continued an additional 16 hours. The mixture was cooled to ambient temperature and 50% aqueous sodium hydroxide solution was added to adjust the pH of the reaction mixture to 7.6. Sodium borohydride (0.11 g, 2.9 mmol) was added and the solution was stirred 3.5 hours at ambient temperature. The reaction mixture was concentrated to 110 mL on a rotary evaporator and isopropyl alcohol (250 mL) was added dropwise over a period of 4 hours to precipitate the product. After cooling the purple slurry to 0° C. for 1 hour, filtration afforded the purple complex of $N^4$-(4-(4-chlorophenyl)benzyl)A82846B (11.03 g, 36.2% potency as wet cake, 3.99 bg, 77.6%.

REFERENCE EXAMPLE B (NO COPPER)

A82846B (0.50 q, 84.3% potency, 0.42 bg, 0.26 mmol) was stirred in 50 mL methanol and 4'-chloro 4-biphenylcarboxaldehyde (72 mg, 0.33 mmol) and pyridine.borane complex (0.033 mL, 0.33 mmol) were added. The mixture was heated at reflux for 6 hours before being cooled to ambient temperature. HPLC analysis of a reaction aliquot afforded a yield of 0.25 g (53.2%) of $N^4$-(4-(4-chlorophenyl)benzyl)A82846B.

EXAMPLE 6

A82846B (0.50 g, 84.3% potency, 0.42 bg, 0.26 mmol was stirred in 50 mL methanol and cupric acetate (45 mg, 0.25 mmol) was added. After stirring at ambient temperature for 10 min, 4'-chloro-4-biphenylcarboxaldehyde (84 mg, 0.39 mmol) and pyridine.borane complex (0.039 mL, 0.39 mmol) were added. The mixture was heated at 57° C. for 24 hours before being cooled to ambient temperature. HPLC analysis of a reaction aliquot afforded a yield of 0.34 g (72.3%) of $N^4$-(4-(4-chlorophenyl)benzyl)A82846B.

EXAMPLE 7

A82846B (0.50 g, 76.3% potency, 0.38 bg, 0.24 mmol) and cupric acetate monohydrate (43 mg, 0.216 mmol) were stirred in 50 mL methanol and 4'-chloro-4-biphenylcarboxaldehyde (84.5 mg, 0.39 mmol) and pyridine.borane complex (0.011 mL, 0.11 mmol) were added. The mixture was heated at 63° C. for 2 hours and an additional portion of pyridine.borane was added (0.01 mL, 0.1 mmol). After 2 hours more at 63° C. a third portion of pyridine.borane (0.005 mL, 0.05 mmol) was added. A fourth portion of pyridine.borane (0.005 mL, 0.05 mmol) was added 2 hours later followed by a fifth portion of pyridine.borane (0.005 mL, 0.05 mmol) after another 5 hours at 63° C. The mixture was heated at 63° C. for another 11 hours before being cooled to ambient temperature. HPLC analysis of a reaction aliquot afforded a yield of 0.34 g (79.2%) of $N^4$-(4-(4-chlorophenyl)benzyl)A82846B.

The reactions reported in Reference Examples A and B and Examples 1–7 were also evaluated (1) for the amount of the remaining starting glycopeptide, (2) for the amount of products alkylated on amine sites other than the $N^4$-position, and (3) for the amount of multiply-alkylated products. The results are set forth in the following table and are expressed as a percentage relative to the intended product monoalkylated on the $N^4$-amine; yields of the intended product are actual yields as recited in the foregoing examples.

TABLE I

| Ex. No. | % Mono-alkyl-ated at $N^4$ | % A82846B | % Mono-alkyl-ated at $N^6$ | % Mono-alkyl-ated at $N^1$ | % Di-alkylated at both $N^4$ and $N^6$ | % Di-alkylated at both $N^1$ and $N^4$ | % Tri-alkylated |
|---|---|---|---|---|---|---|---|
| RE A | 53.7 | 14.1 | 3.5 | 2.4 | 24.4 | 15.9 | 3.4 |
| 1 | 80.3 | 7.6 | 1.0 | 0.4 | 9.7 | 5.6 | 0.7 |
| 2 | 85.4 | 13.0 | 2.4 | 0.7 | 8.2 | 5.9 | 0.9 |
| 3 | 79.1 | 9.8 | 1.1 | 0.5 | 8.1 | 6.4 | 0.6 |
| 4 | 72.9 | 10.1 | 1.0 | 0.4 | 5.8 | 4.7 | 0.3 |
| 5 | 77.6 | 9.3 | 1.0 | 0.4 | 7.1 | 5.4 | 0.5 |
| RE B | 53.2 | 47.6 | 9.9 | 1.3 | 21.7 | 7.8 | 1.8 |
| 6 | 72.3 | 17.8 | 2.1 | 0.7 | 6.2 | 2.5 | 0.4 |
| 7 | 79.2 | 9.2 | 1.4 | 0.3 | 7.4 | 3.4 | 0.3 |

These data show that the present invention provides several advantages. First, the yield of the product alkylated on $N^4$ is increased. Second, the yields of products alkylated on $N^1$ and/or $N^6$ are decreased. Therefore, the present invention provides significant improvement in reaction regioselectivity.

EXAMPLE 8
$N^4$-(4-(4-chlorophenyl)benzyl)A82846B Copper Complex

A82846B (0.50 g, 75.6–78.8% potency, 0.24–0.25 mmol) was stirred in 50 mL methanol and cupric acetate (53–56 mg, 0.29–0.31 mmol) was added followed by 4'-chloro-4-biphenylcarboxaldehyde (70–73 mg, 0.32–0.34 mmol) and sodium cyanoborohydride (20–22 mg, 0.32–0.35 mmol). The reaction mixture was heated at reflux for 24 hours and cooled to ambient temperature. The pH was adjusted to 9.0–9.3 by addition of 1 M NaOH solution. The reaction mixture was concentrated to 10–20 mL on a rotary evaporator and isopropyl alcohol (13–20 mL) was added dropwise to precipitate the purple glycopeptide copper complex which was isolated by suction filtration. Drying in vacuo at 60° C. afforded the glycopeptide copper complex as a purple powder. After four repetitions of the process the combined glycopeptide complex was assayed for copper content and was found to contain 3.0% copper, confirming a 1:1 copper complex with $N^4$-(4-(4-chlorophenyl)benzyl)A82846B.

REFERENCE EXAMPLE C &

EXAMPLES 9–19

Various copper salts were evaluated in a standardized procedure. A82846B (1 equivalent as potency adjusted free base) was stirred in 50 mL methanol and a divalent metal salt (MX2, 0.63 equivalent) or a monovalent metal salt (MX, 1.25 equivalent) was added followed by 4'-chloro-4-biphenylcarboxaldehyde (1.25 equivalent) and sodium cyanoborohydride (1.25 equivalent). The mixture was heated at reflux for 24 hours. After cooling to ambient temperature, an aliquot was removed for HPLC analysis.

The following HPLC System was used for in situ reaction monitoring and yield calculation: HPLC system Waters 600E with HP3395 integrator and Applied Biosystems 757 detector set at 230 nm, sensitivity 0.1 absorption units, 1 sec. filter rise time. Column: DuPont Zorbax SB-Phenyl, 4.6 mm×25 cm. Eluant A: 10% acetonitrile, 90% buffer (0.2% triethylamine, 0.25% $H_3PO_4$). Eluant B: 60% acetonitrile, 40% buffer (0.2% triethylamine, 0.25% H3PO4). Gradient profile at 1 mL/min: initialize 100% A, gradient to 80% A, 20% B over 5 minutes, hold 5 minutes, gradient to 100% B over 20 minutes, gradient to 100% A over 5 minutes, hold 20 minutes. Sample preparation: 0.5–1.0 g of reaction mixture diluted to 25 mL in acetonitrile-buffer. Hold at ambient temperature about 30 minutes until the purple color of the copper complex is discharged. The desired glycopeptide alkylation product elutes at 16–18 minutes, the starting glycopeptide nucleus at 3–4 minutes, the site $N^6$ (monosugar) alkylation product at 18–19 minutes, the site $N^1$ (methyl leucine) alkylation product at 19–21 minutes, dialkylated impurities at 24–26 minutes, and aldehyde at 35–36 minutes. In situ yield is determined by correlation to standards prepared with a reference sample of the product.

The results are shown in the following table. Results for alkylated byproducts are expressed as percentage relative to the desired $N^4$ alkylation product.

TABLE II

| Ex. No. | Salt | Yield (%) | pH | % Relative to Mono on $N^4$ | | |
|---|---|---|---|---|---|---|
| | | | | nucleus | mono on $N^6$ | mono on $N^1$ |
| Ref Ex C | none | 63.5 | 7.2 | 25.6 | 7.8 | 1.8 |
| 9 | $CuF_2$ | 57.8 | 7.2 | 33.3 | 6.2 | 6.1 |
| 10 | $Cu(OH)_2$ | 62.0 | 7.0 | 21.3 | 4.1 | 1.6 |
| 11 | $Cu(OAc)_2$ | 71.7 | 6.4 | 16.9 | 3.6 | 1.8 |

TABLE II-continued

| Ex. No. | Salt | Yield (%) | pH | % Relative to Mono on $N^4$ | | |
|---|---|---|---|---|---|---|
| | | | | nucleus | mono on $N^6$ | mono on $N^1$ |
| 12 | $Cu(O_2CCF_3)_2$ | 64.0 | 6.2 | 17.9 | 4.0 | 2.1 |
| 13 | $Cu(cyclohexanebutyrate)_2$ | 69.0 | 6.4 | 15.6 | 2.3 | 1.2 |
| 14 | $Cu(2-ethylhexanoate)_2$ | 69.0 | 6.5 | 20.8 | 3.1 | 1.4 |
| 15 | $CuCl_2$ | 66.9 | 6.2 | 28.6 | 4.7 | 3.3 |
| 16 | $CuBr_2$ | 67.5 | 6.1 | 18.5 | 3.9 | 2.4 |
| 17 | CuCl | 67.4 | 6.8 | 23.8 | 4.1 | 2.4 |
| 18 | $CuSO_4.5H_2O$ | 33.9 | 5.8 | >100 | 4.6 | 1.9 |
| 19 | $CuSO_4$ | 52.1 | 6.9 | 32.2 | 7.1 | 8.8 |

The same copper salts were further evaluated for their solubility in methanol and for the solubility of the starting glycopeptide antibiotic in their presence. The procedure was as follows: the copper salt (0.165 mmol) was added to 50 mL methanol and stirred at ambient temperature for 15 min. Solubility data was recorded as well as the pH. Glycopeptide nucleus (0.55 g, 74.7% potency, 0.41 bg, 0.26 mmol) was added and stirring continued 15 min. Solubility and pH data was recorded.

TABLE III

| Salt | Salt Solubility in MeOH | pH | nucleus solubility in presence of salt | pH |
|---|---|---|---|---|
| CuF2 | low, cloudy white soln. | 5.9 | slightly, cloudy pink | 7.0 |
| $Cu(OH)_2$ | low, cloudy lite blue soln | 6.2 | slightly, cloudy lite blue | 7.0 |
| $Cu(OAc)_2$ | soluble, clear blue-green | 6.5 | soluble, clear purple | 6.7 |
| $Cu(O_2CCF_3)_2$ | soluble, clear lite blue | 4.4 | soluble, clear purple | 6.2 |
| $Cu(cyclohexane-butyrate)_2$ | faint cloudiness, lite blue-green | 6.0 | soluble, clear purple | 6.7 |
| $Cu(2-ethyl-hexanoate)_2$ | soluble, clear blue-green | 6.5 | soluble, clear purple | 6.7 |
| $CUCl_2$ | soluble, clear colorless | 3.2 | slightly, cloudy purple | 6.6 |
| $CuBr_2$ | soluble, clear yellow | 2.8 | soluble, clear purple | 5.9 |
| $CuSO_4.5H_2O$ | soluble, clear colorless | 3.7 | slightly, cloudy purple | 6.2 |

The foregoing examples illustrate several facets of the present invention. First, copper must be supplied to the reaction mixture in a form which is at least partially soluble. Copper salts such as $CuF_2$ and $Cu(OH)_2$, which are nearly insoluble in methanol, are not effective. Further, the copper salt preferably should allow full solubility of the starting glycopeptide antibiotic, and ideally at the preferred pH. The salts which work the best ($Cu(OAc)_2$, $Cu(cyclohexanebutyrate)_2$, and $Cu(2-ethylhexanoate)_2$) afford complete dissolution of nucleus and afford nucleus solutions at about pH 6.7. The salts which afford improvements over no additive but are not optimal ($Cu(O_2CCF_3)_2$, $CuCl_2$, $CuBr_2$) either afford solubility of nucleus but at less than optimal pH ($CuBr_2$ and $Cu(O_2CCF_3)_2$) or are at optimal pH but do not afford complete nucleus solubility ($CuCl_2$).

In summary, the copper must be in a form which is at least partially soluble, and should allow or maintain full solubility of the starting glycopeptide antibiotic at an acceptable pH, typically 6.3–7. Also, these experiments were conducted with suboptimal amounts of the copper; further advantage from the present invention is obtained at higher copper concentration.

REFERENCE EXAMPLE D (NO COPPER) &

EXAMPLE 20

Two reactions were conducted with the glycopeptide antibiotic A82846A, one without copper (Reference Example D) and one with cupric acetate monohydrate. The aldehyde was 4'-chloro-4-biphenylcarboxaldehyde. The reactions were conducted in the essentially same procedures as reported in the foregoing examples. Results were as set forth in the following table:

TABLE IV

| Reaction | HPLC Area % Yield | % Mono-alkylated on $N^6$ | % Mono-alkylated on $N^1$ | % Di-alkylated on $N^4$ and $N^6$ | % Dialkylated on $N^1$ and $N^4$ |
|---|---|---|---|---|---|
| Ref Ex D | 52.4 | 4.7 | 2.6 | 15.8 | 9.0 |
| Example 20 | 71.4 | 1.1 | 0.9 | 6.6 | 6.0 |

EXAMPLE 21

A82846B Copper Complex

A82846B (3.0 g, 78.7% potency, 2.4 bg, 1.5 mmol) was stirred in 300 mL methanol at ambient temperature and cupric acetate monohydrate (0.31 g, 1.6 mmol) was added. After stirring at ambient temperature for 20 minutes, the purple mixture was heated to 35 to 40° C. and stirred an additional 30 minutes. the solution was concentrated to 45 mL on a rotary evaporator and 100 mL or isopropyl alcohol was added dropwise over 2 hours. The slurry was cooled to 0° C. and filtered. Drying in vacuo at 35° C. afforded 2.6 g of the A82846B copper complex as a purple solid. Mass spectroscopic analysis showed the expected ions for the complex, including a series of peaks around 1653, not seen in the analysis of a reference sample of A82846B, and indicative of the A82846B-copper complex.

Another sample of A82846B copper complex was prepared in like manner and analyzed by UV-visible spectroscopy, which showed an absorbance maxima at about 540 mm, not seen in the spectra of a reference standard of A82846B or of cupric acetate and indicative of the A82846B copper complex.

We claim:

1. An $N^4$ alkylated glycopeptide antibiotic prepared by the steps of (i) reacting a soluble copper complex of a glycopeptide antibiotic having an amine-containing saccharide at $N^4$ with a ketone or aldehyde in the presence of a reducing agent selected from the group consisting of sodium cyanoborohydride and pyridine.borane complex to form a copper complex of said alkylated glycopeptide antibiotic; (ii) isolating said copper complex of said $N^4$ alkylated glycopeptide antibiotic; and (iii) freeing said $N^4$ alkylated glycopeptide antibiotic by aqueous treatment at a pH$\leq$4.

2. The antibiotic of claim 1 wherein said antibiotic is prepared in methanol.

3. The antibiotic of claim 1 wherein said aldehyde or ketone is present in a slight excess.

4. The antibiotic of claim 1 wherein said reducing agent is present in at least an equimolar amount.

5. The antibiotic of claim 1 wherein said soluble copper complex in step (i) is a 1:1 copper complex with A82846B.

6. The antibiotic of claim 5 wherein said aldehyde is 4'-chloro-4-biphenylcarboxaldehyde.

7. The antibiotic of claim 1 wherein said antibiotic is prepared at a pH between 6 and 8.

8. The antibiotic of claim 7 wherein said pH is between 6.3 and 7.0.

9. The antibiotic of claim 1 wherein said soluble copper complex in step (i) is prepared by adding a source of soluble copper to a glycopeptide antibiotic having an amine-containing saccharide at $N^4$.

10. The antibiotic of claim 9 wherein said source of soluble copper is copper (II) acetate.

11. A copper-antibiotic complex consisting essentially of copper and with a reductively alkylated glycopeptide antibiotic prepared by reacting a soluble copper complex of a glycopeptide antibiotic having an amine-containing saccharide at $N^4$ with a ketone or aldehyde in the presence of a reducing agent selected from the group consisting of sodium cyanoborohydride and pyridine.borane.

12. The copper-antibiotic complex of claim 11 wherein said aldehyde is 4'-chloro-4-biphenylcarboxaldehyde.

13. The copper-antibiotic complex of claim 11 wherein said glycopeptide antibiotic having an amine-containing saccharide at $N^4$ is selected from the group consisting of A82846A, A82846B, A82846C and orienticin A.

14. The copper-antibiotic complex of claim 13 wherein said glycopeptide antibiotic having an amine-containing saccharide at $N^4$ is A82846B.

15. The copper-antibiotic complex of claim 14 wherein said aldehyde is 4'-chloro-4-biphenylcarboxaldehyde.

* * * * *

UNITED STATES PATENT AND TRADEMARK OFFICE
CERTIFICATE OF CORRECTION

PATENT NO.    : 5,998,581

DATED         : December 7, 1999

INVENTOR(S)   : Richard Alan Berglund, Nancy Anne Lockwood, Howard Eugene Magadanz, Hua Zheng It is certified that an error appears in the above-identified patent and that said Letters Patent is hereby corrected as shown below:

Column 18, line 29 reads " . . .copper and with a reductively. . ." should read -- . . .copper and a reductively. . . --

Signed and Sealed this

Fourteenth Day of November, 2000

Attest:

Q. TODD DICKINSON

*Attesting Officer*        *Director of Patents and Trademarks*